United States Patent [19]

Sujansky et al.

[11] Patent Number: 4,499,183
[45] Date of Patent: Feb. 12, 1985

[54] DETECTING INTRACELLULAR ANTIGENS IN SWELLED AND FIXED CELLS WITH LABELED ANTIBODY

[75] Inventors: Daniel J. Sujansky, Manville; Martha W. Rancourt, Piscataway, both of N.J.

[73] Assignee: Ortho Diagnostic Systems Inc., Raritan, N.J.

[21] Appl. No.: 451,675

[22] Filed: Dec. 21, 1982

[51] Int. Cl.³ .................... G01N 33/54; G01N 33/50
[52] U.S. Cl. .......................................... 435/6; 424/3; 435/7; 435/810; 436/508; 436/804; 436/805; 436/808
[58] Field of Search ............... 435/6, 7, 810; 436/508, 436/804, 805, 808; 424/3

[56] References Cited

U.S. PATENT DOCUMENTS 3,864,212  2/1975  Berkhan .......................... 436/508 X
4,296,201  10/1981  Ax .................................. 436/508 X
4,307,189  12/1981  Kit ........................................... 435/6

OTHER PUBLICATIONS

Chemical Abstracts, 97:211108y (1982).
Castella, A. et al., Terminal Deoxynucleotidyl Transferase Activity in Non-Hematologic and Hematologic Neoplasms, Annals of Clinical and Laboratory Science, vol. 12, No. 5:403–407 (1982).
Kung, P. C., et al., Terminal Deoxynucleotidyltransferase, Biological Chemistry, vol. 251, 8:2399–2404 (4/25/76).
Cibull, M. L. et al., Evaluation of Methods of Detecting Terminal Deoxynucleotidyl Transferase in Human Hematologic Malignancies, A. J. C. P., vol. 77, No. 4:420–423 (Apr. 1982).
Szabo, G. et al., Permeabilization of Lymphocytes with Polyethylene Glycol 1000, Discrimination of Permeabilized Cells by Flow Cytometry, Cytometry, vol. 3, No. 1:59–63 (1982).
Sterns, M. E. et al., A Functional In Vitro Model for Studies of Intracellular Motility in Digitonin-permeabilized Erythrophores, J. Cell Biology, vol. 94:727–739 (Sep., 1982).
Obara, Y. et al., Chromosome Investigations of the Usubuchi Sarcoma, Cytologia 46:413–426 (1981).
Nidas ™ IFA-ANA Test Kit for Determinations of Antinuclear Antibodies, product insert from Fisher Diagnostics.
BRL ™ TdT, Terminal Deoxynucleotidyl Transferase Immunofluorescent Assay System, product insert from BRL.
BRL ™ Terminal Transferase Immunofluorescent Assay Kit, product insert from BRL prior to 11/82.

*Primary Examiner*—Sidney Marantz
*Attorney, Agent, or Firm*—Mark A. Hofer

[57] ABSTRACT

Methods and reagent kits for the detection of intracellular antigens such as TdT and antinuclear antibodies. The methods involve swelling the cells with a hypotonic solution for increasing the localization of large molecular weight substances such as antibodies at intracellular antigenic sites, fixing the cells and reacting them with antibodies specific for the intracellular antigen to be detected. The cells are then further reacted with labeled antibody specific for the first antibody, washed to remove unreacted antibodies and the presence of label detected whereby the presence or absence of the intracellular antigen may be determined.

24 Claims, No Drawings

DETECTING INTRACELLULAR ANTIGENS IN SWELLED AND FIXED CELLS WITH LABELED ANTIBODY

FIELD OF THE INVENTION

This invention relates generally to the field of immunoassays and specifically provides new methods and reagent kits for the detection of intranuclear antigens as well as antibodies directed against defined intracellular antigens.

BACKGROUND OF THE INVENTION

With the press of scientific research in the area of cancer diagnosis and the relatively recent developments involving antibodies in general and monoclonal antibodies specifically, significant advancements in the field of immunoassays have been and are continuing to be made. For instance, the development of monoclonal antibodies, i.e. a purified population of specifically reactive biological molecules, permits specific targeting for particular antigens by virtue of their manner of production and selection. This allows the development and identification of antigenic maps which describe and characterize both normal and abnormal cells. The invention described later is capable of employing both monoclonal and polyclonal antibodies.

For instance, it has been discovered that the presence of terminal deoxynucleotidyl transferase (TdT), an enzyme that can polymerize deoxynucleotides onto a primer in the absence of a template, serves as a useful indicator for the differential diagnosis of some hematologic malignancies and disorders. For example, TdT has been found absent in cells from non-hematologic tumors, Hodgkin's lymphoma, B cell lymphoproliferative disorders, peripheral T cell neoplasms, reactive lymphadenopathy, and acute nonlymphocytic leukemia. In contrast, non-T non-B cell acute lymphocytic leukemia, T cell acute lymphocytic leukemia, T cell lymphoblastic lymphoma and chronic granulocytic leukemia in blast crisis have been noted to contain marked TdT activity. For a discussion see: Castella et al, "Terminal Deoxynucleotidyl Transferase Activity in Non-Hematologic and Hematologic Neoplasms", Annals of Clinical and Laboratory Science, Vol. 12, No. 5:403–407 (1982). Such a differential diagnosis is particularly useful for monitoring relapses of acute lymphocytic leukemia as well as for predicting patient response to Vincristine and Prednisone therapy treatments.

Other autoimmune connective tissue diseases produce a spectrum of autoantibodies having specificity for a variety of nuclear antigens. Generally, the antinuclear antibodies (ANA hereafter) may belong to any of the classes of immunoglobulins (IgM, IgG, IgA, IgD, and IgE) and are not species-specific. ANAs often demonstrate specificity for one or several different nuclear antigens including deoxynucleoprotein, single and double stranded DNA, nucleoli including nucleolar ribonucleoprotein, histones, and saline-extractable antigens. The presence of antinuclear antibodies has long been recognized as a symptom of systemic lupus erythematosus (SLE). Other conditions that produce ANA include scleroderma, Sjogrens Syndrome, dermatomyositis, rheumatoid arthritis, polymyositis, and mixed connective tissue disease.

Consequently, it is quite clear that the development of tests for detecting the presence of specified intranuclear antigens such as TdT as well as antinuclear antibodies is of great significance in the clinical environment. One such technique for the detection of TdT is described by Kung et al in an article entitled "Terminal Deoxynucleotidyltransferase", Biological Chemistry, Vol. 251, 8:2399–2404 (4/25/76). That article describes a competitive type radioimmunoassay using $^{125}I$-labeled pure enzyme and antisera for the detection and quantitation of calf terminal-transferase. Such a method, however, disadvantageously requires radioisotopes necessitating careful handling as well as the obvious associated spectrum of risks and disadvantages entailed therewith. Further, such a method provides data in the form of nanograms of enzyme/milligram of cell protein but gives no information regarding the presence or absence of enzymes or intranuclear antigens within cells and cell types.

It is an object of the present invention to provide both methods and reagents for the determination and localization of intranuclear antigens in general and TdT specifically, within cells of a mixed cell population without relying on radioisotopes.

An indirect immunofluorescence method has also been described in the Castella et al article cited above. Although this method does provide some differential information with regard to the presence of TdT within cells, it disadvantageously is limited to microscopic preparations involving glass slides. Further, the procedure described requires an incubation of the cells with highly concentrated TdT specific antibody thereby greatly increasing expense without a concomitant increase in sensitivity, which parameters are important criteria within the typically over-burdened clinical environment.

It is an object of the present invention to substantially reduce the heretofore previously required high antibody concentrations thereby greatly reducing cost and to obtain substantially the same or greater sensitivity.

It is yet another object of the present invention to provide methods and reagents which may be used in flow cytometry apparatus such as the type described in U.S. Pat. Nos. 4,284,412 to Hansen et al, 3,705,771 to Friedman et al, 4,202,625 to Weiner et al, 4,284,355 to Hansen et al and 4,325,706 to Gershman et al, all of which are incorporated herein by reference, whereby large numbers of cells in a sample containing a mixed population of cells may be analyzed very rapidly and with high accuracy by utilizing hydrodynamic focusing, focused light sources and light scatter and/or fluorescence detectors with appropriate electronic analysis.

Another article by Cibull et al, "Evaluation of Methods of Detecting Terminal Deoxynucleotidyl Transferase in Human Hematologic Malignancies", A. J. C. P. Vol. 77, No. 4:420–423 (April 1982) provides the results of a correlation study comparing the specificity and sensitivity of an immunofluorescence technique, such as that of Kung et al described above, with a biochemical assay technique for determining enzymatic activity. The reference does indicate that although the radiometric assay and the immunofluorescence method do not reflect equivalent data, each method provides useful diagnostic criteria despite the fact that the significance of the difference in data is still not completely understood.

Typically, the conventional fluorescent methods for detecting either TdT such as those supplied by BRL (Bethesda Research Laboratories) or for detecting ANA such as the Nidas Test Kit available from Fisher Diagnostics, have uniformly relied on significant volumes and high concentrations of antibody reagents in order to overcome sensitivity limitations. These limitations have heretofore been the result of relatively slow and diminished cellular uptake.

It is yet another object of the present invention to provide methods for detecting intranuclear antigens, intracellular antigens, and ANAs which overcome limitations heretofor characteristic of conventional methods. Such a goal is particularly laudatory in view of the, as yet, relatively expensive and limited supply of antibodies having the required degree of specificity and affinity or binding capacity. The reduction in cost of such test kits is therefore a related object of the present invention.

SUMMARY OF THE INVENTION

Accordingly, there are provided methods for the detection of intracellular antigens which would include hormones, enzymes, and other antigens associated with internal organelles of the cell and intranuclear antigens such as enzymes, DNA, and RNA as well as methods for the detection of ANAs. It has been discovered by the inventors hereof that to accomplish these methods the cells must be contacted with a hypotonic solution carefully adjusted to swell the cells but not to result in substantial lysis prior to the completion of the assay, specifically the detection step. Swelling the cells results in an expanded cell size and, it is believed by the inventors, larger cell membrane channels for facilitating antibody uptake. Thereafter, the cell membrane is rigidized and water is removed by standard fixation techniques. The cell is preferably first hydrated and then under appropriate conditions, reacted with a solution containing antibodies specific for the antigen or, in the case of ANA, antibody to be detected. In the latter case, the antibody is advantageously labeled with a detectable label such as with a fluorochrome, metal particle, radioisotope or enzyme whereas in the former case, an indirect immunofluorescence technique is preferably employed. This is accomplished by subsequent reaction of the cells previously reacted with the first antibody, with a second antibody specific for the first antibody. The second antibody is ideally labeled with a detectable label as above. Those antibodies not attached either directly or indirectly (i.e., by attachment through another antibody in turn attached to the antigen or antibody) to the ANA, intracellular or intranuclear antigen of interest are advantageously removed by a washing process and the remaining cells analyzed for the presence of label. Detection of the label is in turn related to the presence of the intranuclear antigen, intracellular antigen or ANA to be detected.

An ideal reagent kit in accordance with this discovery would therefore comprise a swelling solution, as well as antibody specific for the antigen to be detected, second antibody with a label such as fluorescein isothiocyanate (FITC) specific for the first antibody and various controls and washing buffers.

DETAILED DESCRIPTION OF THE INVENTION AND BEST MODE

This invention is predicated upon the surprising discovery that an intranuclear antigen such as TdT (some investigators believe TdT can also be found intracellularly and is not intranuclearly limited) may be readily detected with a greatly reduced concentration of antibody if the cell membranes are first treated with a hypotonic solution in order to swell the membrane. Such altered membranes apparently facilitate entry of the antibody molecules thereby resulting in more efficient utilization of the antibodies. Although swelling of cells has been known for quite some time, use thereof has been previously unknown in the context of an immunoassay designed for the detection of intracellular antigens or ANAs.

For instance, polyethylene glycol has been employed to improve discrimination between viable and nonviable cells stained directly with a fluorescent dye such as acridine orange. Discrimination between live and dead cells is particularly important in the monitoring of cytotoxicity of drug therapy. See Szabo et al, "Permeabilization of Lymphocytes with Polyethylene Glycol 1000. Discrimination of Permeabilized Cells by Flow Cytometry", Cytometry, Vol. 3, No. 1:59–63 (1982).

Another study employed 0.001% digitonin for the purpose of permeabilizing membranes, specifically those of fish chromatophores, in order to study cyclic aggregation and dispersion of pigment molecules in those erythrophores. See Stearns et al, "A Functional In Vitro Model for Studies of Intracellular Motility in Digitonin-permeabilized Erythrophores", J. Cell Biology, 94:727–739 (9/1982).

Hypotonic solutions for swelling cells have been employed in karyology. For instance, in an article by Obara et al, "Chromosome Investigations of the Usubuchi Sarcoma", Cytologia 46:413–426 (1981), a cytogenetic study of Usubuchi Sarcoma (a methylcholanthrene-induced rat ascites tumor) is described. Therein, the cells were swelled by hypotonic treatment with KCl in order to separate the chromosomes, the cells fixed, and the chromosomes banded with conventional staining such as urea-Giemsa technique for G-bands. It is important to note, however, the hypotonic solutions used in this study, as well as those employed in conventional karyologic studies, are adjusted in order to swell the cell until it lysis. In effect, the cell is treated so that it "explodes", thereby dispersing and separating the chromosomes for ease of study. The present invention avoids these destructive results of a clearly disadvantageous nature vis-a-vis immunoassays by carefully altering the hypotonicity of the swelling solution in order to optimize swelling and yet avoid substantial lysis prior to completion of the immunoassay. Thus, intact cells can be provided for clinical evaluation either by microscopic slide or by flow cytometry methods. For instance, a preferred formulation of an ideal hyptonic solution would be 0.1 molar KCl.

EXAMPLE 1

Method For Detecting TdT In A Slide Assay Format

Lymphocytes from a patient blood sample are prepared over a density gradient such as Ficoll-Hypaque ™ (available from Pharmacia Corp.) or Lymphoprep ™ (available from Nyegaard and Co. A/S, Oslo, Norway) pursuant to the instructions therewith and a cell count performed after the final wash. Approximately $2 \times 10^6$ cells are added to a clean $10 \times 75$ mm test tube and the cells pelleted using a Clay-Adams Serofuge ™ for 1 minute (3440 rpm–1000 g). All of the supernatant except for 1 drop is decanted; the last drop is employed to resuspend the cells. 1 ml of a 0.1 M solution of KCl is added to the resuspended cells and mixed by vortexing. After incubation at room temperature for 5 minutes, the cells are pelleted and the supernatant decanted as above. An aliquot of the suspension is pipetted by pasteur pipette onto a glass slide and air dryed. The cells are fixed on the slide in absolute methanol at 5° C. for 30 minutes. The fixed cells are rehydrated by flooding the slide with PBS (phosphate buffered salt solution) for 5 minutes at room temperature and excess PBS removed without permitting the cells to dry out. In one area of the slide, 15 ul of anti-TdT antibody is applied and over another area of the slide, 15 ul of the control antibody is applied. The slides are incubated at room temperature for 30 minutes in a humid chamber and then immersed completely within a Copeland jar for washing in PBS. One change of PBS is made after 2½ minutes for a total wash time of 5 minutes. Excess PBS is removed from the slides by shaking and 15 ul of labeled second antibody specific for the first antibody is applied over both areas of the slide. The slide is reincubated at room temperature for 30 minutes in a humid chamber and washed in the Copeland jar as before. The slides are then air dried and a cover slip placed with a drop of mounting fluid over each area. Nail polish is employed to seal the cover slip and the slide is examined for fluorescence. Presence of fluorescence within the confines of the cell membrane, i.e., the interior of the cell, indicates the presence of TdT within that cell. Other intracellular antigens may be likewise detected by appropriate substitution of the anti-TdT antibody with an antibody specifically reactive with the intracellular antigen of interest.

EXAMPLE 2

Method For Determining The Presence Of TdT In An Assay Format Suitable For Use In A Flow Cytometer Lymphocytes are prepared in the manner as provided in Example 1. Two $10 \times 75$ mm disposable test tubes are precoated with PBS-BSA (BSA=bovine serum albumin) and labeled test and control by adding 3 mls of PBS-BSA to each of the test and control tubes for 5 minutes at room temperature and then aspirated off whereby attachment of the cells to the glass is inhibited. A 1 ml aliquot of cell suspension contaning $1 \times 10^6$ cells is added to both tubes. The cells are pelleted in a Serofuge ™ for 90 seconds at room temperature and the supernatant carefully removed using a pasteur pipette in order to avoid disturbing the cell button. The cells are resuspended in 0.5 ml of a 0.1 M hypotonic solution of KCl and incubated at room temperature for 5 minutes. 0.5 ml of absolute methanol is added to the suspension and incubated at room temperature for 30 minutes with gentle vortexing every 10 minutes. The cells are pelleted and the supernatant removed as above. The cells are then washed with 0.5 ml of PBS, again pelleted and the supernatant removed. 50 ul of anti-TdT antibody is added to the labeled test tube and 50 ul of IgG control antibody is added to the control test tube. The tubes are gently shaken to resuspend the cell pellet and placed at 37° C., either in a warm air incubator or water bath, for 30 minutes. The tubes are gently agitated every 10 minutes to resuspend the cells. The cells are then washed with PBS, pelleted and the supernatant removed. This washing step is repeated and 50 ul of FITC labeled second antibody, reactive against the first antibody, is added to both tubes. The cell pellet is resuspended and the tubes placed at 37° C. for 30 minutes with agitation every 10 minutes to resuspend cells. The cells are washed in PBS, pelleted and the supernatant removed as above. The cells are then washed with 0.1% BSA having as a preservative 0.1% $NaN_3$ in PBS, pelleted and the supernatant aspirated. The cells are resuspended in 0.1% BSA with 0.1% $NaN_3$ in PBS and analyzed via flow cytometry on an ORTHO SPECTRUM III ™ available from Ortho Diagnostic Systems Inc., Raritan, N.J. The ORTHO SPECTRUM III ™ Laser Flow Cytometry System is capable of measuring the fluorescent and light scattering signals of individual hydrodynamically focused cells bearing antigens (e.g. TdT) labeled by means of labeled antibodies within a population of mixed cells. As with Example 1, appropriate antibody substitution permits identification of other intracellular antigens.

EXAMPLE 3

Alternative Procedure To The Above Preferred Embodiments For Localization Of TdT An aliquot containing $1 \times 10^6$ cells is placed into a Fisher Model 59 centrifuge tube and the cells pelleted via centrifugation in a Fisher Model 59 ™ centrifuge at 2000 g for 90 seconds. The supernatant is removed and the cell pellet resuspended in 0.5 ml of a 0.1 M hypotonic solution of KCL and incubated for 5 minutes at 20°–22° C. The cells are repelleted and the supernatant removed as above. The cells are resuspended in fixative comprising a 50:50 mix of absolute methanol to PBS for 30 minutes at room temperature. The cells are repelleted and washed in PBS resuspended in 0.035 ml of appropriately diluted anti-TdT antibody, and then incubated at 37° C. for 30 minutes with occasional mixing. Thereafter, the cells are washed two times in PBS and resuspended in 0.035 ml of FITC IgG antibody reactive with the first antibody. For example, the first antibody may be a rabbit anti-TdT antibody and the second antibody may be a goat anti-rabbit antibody. The cells containing the second antibody are incubated at 37° C. for 30 minutes and then washed two times in PBS. The cells are resuspended in 1 ml PBS for flow cytometry analysis. For microscopic viewing, 1 drop of the suspension may be placed onto a glass slide and air dried. Thereafter, a drop of Difco FA mounting fluid pH 7.2 is added and a cover slip applied.

It may be readily appreciated that the advantages of treating cells as described above, as compared to conventionally treated cells include the increased localization of antibodies at intracellular antigenic sites as measured by flow cytometry (quantitative) combined with the flexibility of examination by microscopy (qualitative). Although it is noted that the swelling procedures result in a larger cell diameter thereby typically raising the forward scatter peak in a flow cytometry apparatus such as that described, this is a constant error and may be easily compensated for or safely ignored. As expected, the flow cytometry procedure permits rapid and accurate characterization of small segments of a large, diversified population of cells.

Antibodies specific for TdT may be readily acquired from a number of commercial sources including Bethesda Research Labs (BRL), and PL Biochemicals. Alternatively, such antibodies to TdT or other antigens can be produced using conventional polyclonal or monoclonal techniques commonly known. Similarly, antibodies to the anti-TdT antibody may be readily acquired from Tago or produced and labeled with a detectable label using methods and techniques well known in the conventional art. Such labels may, of course, include fluorochromes, enzymes which in the presence of a substrate produce a detectable product, radioisotopes, metal particles such as gold particles and the like.

One reading this disclosure and skilled in the art can readily appreciate the minor alterations required in the above techniques to detect ANAs. Using the swelling techniques described on reagent test cells makes them more receptive to the uptake of ANAs present in a body fluid sample. Subsequent detection of the ANAs may be accomplished with an indirect fluorescent antibody technique as afore-described.

It may be readily appreciated that a tremendous advantage of the described procedures is the significant reduction in the amount of primary antibody required since the efficiency with which that antibody is utilized (i.e., by cellular uptake) is greatly increased. In fact, dilutions of two times or more of solutions previously required in prior techniques may be accomplished without any significant loss in detectable levels of intracellular localization of the antibody.

It may be readily appreciated by one skilled in the art that various modifications and alterations may be made to the above methods and reagents such as substituting sodium citrate for KCl, etc., without departing from the spirit and scope of the invention.

We claim:

1. A method of detecting intracellular antigens selected from the group consisting of hormones, enzymes, DNA, RNA, immunoglobulins, drugs, and organelle associated antigens in whole cells comprising the steps of contacting the cells with a hypotonic solution whereby the cells swell in size but step; fixing the cells whereby the cell membranes are rigidized and water is removed; hydrating and reacting the cells under conditions permitting immunological reactions with specific for the antigen to be detected and having a detectable label; washing to remove antibodies which have not reacted with the antigen to be detected; and detecting the presence of said label whereby the absence or presence of the antigen to be detected may be determined.

2. The method as provided in claim 1 wherein the label is selected from the group consisting of fluorophores, radioisotopes, enzymes, metal particles and light scattering substances.

3. The method as provided in claim 1 wherein the label is an enzyme and before the detecting step, substrate is added whereby detectable product is produced by the action of said enzyme on said substrate.

4. The method as provided in claim 1 wherein the detecting step is accomplished by placing the cells after the washing step into a flow cytometry apparatus which hydrodynamically focuses the cells, illuminates the cells by a focused light source, and detects the presence of said label by detecting the resultant altered light characteristics occasioned by said label.

5. The method as provided in claim 1 wherein the antigen to be detected is TdT.

6. The method as provided in claim 5 wherein the antibody is rabbit anti-TdT antibody.

7. A method for determining the presence of antibodies specific for intracellular related antigens in a sample comprising the steps of: providing cells having intracellular antigens with which the antibodies to be detected can react; contacting said cells with a hypotonic swelling solution whereby the cells swell in size but substantially do not lyse prior to the completion of the detecting step; fixing the cells by further contacting said cells with a fixing solution whereby the cell membrane is rigidized and water is removed; hydrating and reacting the cells with the sample containing the antibodies to be detected; further reacting the cells with a second antibody having a detectable label attached thereto and specific for the antibodies to be detected; and detecting the presence of label for only those labeled antibodies which have reacted with the antibodies to be determined and which have in turn have reacted with the intracellular antigens of said cells.

8. The method as provided in claim 7 wherein the label is an enzyme and before the detecting step, substrate is added whereby detectable product is produced by the action of said enzyme on said substrate.

9. The method as provided in claim 7 wherein the label is selected from the group consisting of fluorophores, radioisotopes, enzymes, metal particles and light scattering substances.

10. The method as provided in claim 9 wherein the detecting step further comprises washing said cells to remove unreacted labeled antibodies whereby detection of only those labeled antibodies which have reacted with the antibqdies specific for the intracellular antigens is realized.

11. The method as provided in claim 10 wherein the detecting step is accomplished by adding said sample to flow cytometry apparatus which hydrodynamically focuses the cells, passes the cells past a focused light source, and detects the label by the resultant altered light characteristics of the cells whereby the presence of antibodies specific for intracellularly related antigens may be determined.

12. A reagent test kit for determining the presence of intracellular TdT by detecting an antibody associated label comprising in separate containers:
(a) first antibody specific for TdT;
(b) FITC labeled second antibody specific for the first antibody; and
(c) swelling solution having a hypotonicity adjusted to swell the cells but not substantially lyse the cells prior to completion of the label detecting step of the test.

13. The reagent kit as provided in claim 12 further comprising:
(a) control antibodies with which the reactivity of the first antibody can be monitored; and
(b) coating and wash buffers in a form selected from the group consisting of preweighed dry chemicals for addition to water and premixed, aqueous solutions.

14. A reagent test kit for determining the presence of antinuclear antibodies comprising in separate containers:
(a) cells having nuclear antigens with which the antinuclear antibodies can react;
(b) FITC labled antibodies specific for the antinuclear antibodies; and
(c) swelling solution having a hypotonicity adjusted to swell the cells but not substantially lyse cells prior to completion of the test.

15. A method for determining the presence of, in a sample containing cells, antibodies which are specific for and have reacted with intracellularly located antigens comprising the steps of providing a sample containing cells suspected of having intracellular antibodies which have previously reacted with intracellularly located antigens; contacting said cells with a hypotonic swelling solution whereby the cells swell in size; reacting said swollen cells with labeled antibodies specific for the antibodies whose presence is to be determined whereby an antibody complex is formed; detecting the presence of only labeled antibody complexes.

16. The method as provided in claim 15 wherein the label is selected from the group consisting of fluorophores, radioisotopes, enzymes, metal particles and light scattering substances.

17. The method as provided in claim 15 wherein the label is an enzyme and before the detecting step, substrate is added whereby detectable product is produced by the action of said enzyme on said substrate.

18. A method for detecting intracellular antigens selected from the group consisting of hormones, enzymes, DNA, RNA, immunoglobulins, drugs and organelle associated antigens in whole cells comprising the steps of contacting the cells with a hypotonic solution whereby the cells swell in size but substantially do not lyse prior to completion of the detecting step; fixing the cells whereby the cell membranes are rigidized and water is removed; hydrating and reacting the cells under conditions permitting immunological reactions with a first antibody specific for the antigen to be detected; further reacting said cells with a second antibody specific for said first antibody and having a detectable label associated therewith; washing to remove antibodies which have not reacted immunologically; and detecting the presence of said label whereby the absence or presence of the antigen to be detected may be determined.

19. The method as provided in claim 18 wherein the label is selected from the group consisting of fluorophores, radioisotopes, enzymes, metal particles and light scattering substances.

20. The method as provided in claim 18 wherein the label is an enzyme and before the detecting step, substrate is added whereby detectable product is produced by the action of said enzyme on said substrate.

21. The method as provided in claim 18 wherein the detecting step is accomplished by placing the cells, after the washing step, into a flow cytometry apparatus which hydrodynamically focuses the cells, illuminates the cells by a focused light source, and detects the presence of said label by detecting the resultant altered light characteristics occasioned by said label.

22. The method as provided in claim 18 wherein the antigen to be detected is TdT.

23. The method as provided in claim 22 wherein the first antibody is rabbit anti-TdT antibody.

24. The method as provided in claim 23 wherein the second antibody is goat anti-rabbit antibody.

* * * * *

UNITED STATES PATENT AND TRADEMARK OFFICE
CERTIFICATE OF CORRECTION

PATENT NO. : 4,499,183

DATED : February 12, 1985

INVENTOR(S) : Surjansky, et al.

It is certified that error appears in the above-identified patent and that said Letters Patent is hereby corrected as shown below:

Front Page: Other Publications, second to last cite:

delete "insert from BRL" and insert -- insert from BRL, received 11/5/82 --.

In the Claims:

Claim 1, line 26, delete "A method of" and insert -- A method for --.

Claim 1, line 31, delete "but step; fixing " and insert -- but substantially do not lyse prior to completion of the detecting step; fixing --.

Claim 1, line 34, delete "reactions with specific " and insert --     reactions with an antibody specific --.

UNITED STATES PATENT AND TRADEMARK OFFICE
CERTIFICATE OF CORRECTION

PATENT NO. : 4,499,183
DATED : February 12, 1985
INVENTOR(S) : Surjansky, et al.

It is certified that error appears in the above-identified patent and that said Letters Patent is hereby corrected as shown below:

Claim 10, line 21, delete "antibqdies" and insert
-- antibodies --.

Signed and Sealed this

Twenty-sixth Day of August 1986

[SEAL]

Attest:

Attesting Officer

DONALD J. QUIGG

Commissioner of Patents and Trademarks